(12) United States Patent  (10) Patent No.: US 7,856,673 B2
Reed  (45) Date of Patent: Dec. 28, 2010

(54) GOGGLES WITH INTERCHANGEABLE LENS

(75) Inventor: Russell Reed, Park City, UT (US)

(73) Assignee: Cross Optical Group, Inc., Daytona Beach, FL (US)

( * ) Notice: Subject to any disclaimer, the term of this patent is extended or adjusted under 35 U.S.C. 154(b) by 831 days.

(21) Appl. No.: 11/779,331

(22) Filed: Jul. 18, 2007

(65) Prior Publication Data

US 2009/0019620 A1  Jan. 22, 2009

(51) Int. Cl.
*A61F 9/02* (2006.01)

(52) U.S. Cl. .................. 2/441; 2/438; 351/83; 351/103

(58) Field of Classification Search .................. 2/1, 2/69, 12, 13, 15, 425, 426, 429, 438, 441, 2/443, 444.445, 446, 453; 351/83–88, 131
See application file for complete search history.

(56) References Cited

U.S. PATENT DOCUMENTS

| | | | |
|---|---|---|---|
| D84,596 S | 7/1931 | Rohman | |
| 2,403,223 A | 7/1946 | Kaesz | |
| D146,004 S | 12/1946 | Jacobson | |
| D146,602 S | 4/1947 | Jaffe | |
| D149,312 S | 4/1948 | Schwartz | |
| D151,070 S | 9/1948 | Rohman | |
| D151,222 S | 10/1948 | Ditto | |
| 2,482,195 A | 9/1949 | Martin | |
| D155,580 S | 10/1949 | Coen | |
| D170,745 S | 11/1953 | Carmichael | |
| D173,868 S | 1/1955 | Belgard | |
| 2,749,800 A * | 6/1956 | Gagnon | 351/91 |
| 2,781,693 A * | 2/1957 | Brumby | 351/85 |
| D185,987 S | 8/1959 | Marfuggi | |
| D192,884 S | 5/1962 | Petitto | |
| D193,028 S | 6/1962 | Petitto | |
| 3,052,160 A | 9/1962 | Ratti | |
| D202,658 S | 10/1965 | Petitto | |
| D204,812 S | 5/1966 | Schindler | |
| D207,028 S | 2/1967 | Griss | |
| D209,861 S | 1/1968 | Demmel | |

(Continued)

OTHER PUBLICATIONS

Fathom, Glass Mirror Lens. Costa Del Mar. Downloaded Dec. 7, 2006 at http://www.eyeglasses.com/product/1091472073-1091472073.

*Primary Examiner*—Katherine Moran
*Assistant Examiner*—Richale L Quinn
(74) *Attorney, Agent, or Firm*—Malloy & Malloy, P.A.

(57) ABSTRACT

The goggles of the invention utilize a substantially rigid frame with separate top and bottom individually rotatable elements, namely an upper browbar and a lower nosepiece, that firmly capture the lens from above and below. The lens is further secured to the frame by projections on each of the browbar and nosepiece which fit through apertures in the lens. At the top, a post which projects forwardly from the frame is received in the well of the browbar by snap-fit engagement. At the bottom, a prong on the rotatable nosepiece passes through a bottom aperture of the lens and is received in a recess of a bottom portion of the frame by snap-fit engagement. The apertures and cooperating projections are preferably located along the center of a one-piece lens. Thus, the rotatable browbar and nosepiece capture the lens top and bottom by edgewise compression and hold the lens front-to-back.

13 Claims, 4 Drawing Sheets

U.S. PATENT DOCUMENTS

| | | |
|---|---|---|
| D209,862 S | 1/1968 | McCracken |
| D210,697 S | 4/1968 | Ramp |
| D210,698 S | 4/1968 | Simon |
| 3,395,406 A * | 8/1968 | Smith ............................ 2/436 |
| D213,595 S | 3/1969 | Simon |
| D216,563 S | 2/1970 | Ramp |
| D218,128 S | 7/1970 | Bloch |
| D218,953 S | 10/1970 | Maiese |
| D220,289 S | 3/1971 | Mitchell |
| D220,291 S | 3/1971 | Leominster |
| D227,405 S | 6/1973 | Shindler |
| D232,380 S | 8/1974 | Johnsen |
| D243,084 S | 1/1977 | Johnsen |
| 4,222,640 A | 9/1980 | Bononi |
| D263,058 S | 2/1982 | Johnsen |
| 4,345,824 A * | 8/1982 | Daubignard ................. 351/98 |
| D285,020 S | 8/1986 | Schmidthaler |
| D290,465 S | 6/1987 | Levoy |
| D300,226 S | 3/1989 | Ramp |
| D321,523 S | 11/1991 | Cherian |
| D324,394 S | 3/1992 | Jannard |
| 5,343,259 A | 8/1994 | Nakanishi |
| 5,373,331 A * | 12/1994 | Vallalla et al. ................ 351/57 |
| 5,423,092 A * | 6/1995 | Kawai ............................ 2/441 |
| D369,375 S | 4/1996 | Jannard et al. |
| D369,376 S | 4/1996 | Guo |
| D371,384 S | 7/1996 | Bonnemere |
| 5,541,674 A | 7/1996 | Jannard et al. |
| D372,929 S | 8/1996 | Conway |
| D376,810 S | 12/1996 | Ohie |
| 5,608,469 A | 3/1997 | Bollé |
| D380,487 S | 7/1997 | Nevitt |
| D382,291 S | 8/1997 | Wilson |
| D382,892 S | 8/1997 | Murai |
| D383,478 S | 9/1997 | Wilson |
| D385,291 S | 10/1997 | Jannard et al. |
| D391,596 S | 3/1998 | Simioni |
| D393,653 S | 4/1998 | Howard, IV |
| D394,871 S | 6/1998 | Simioni |
| 5,764,333 A | 6/1998 | Somsel |
| D397,350 S | 8/1998 | Jannard et al. |
| D397,712 S | 9/1998 | Simioni |
| D398,022 S | 9/1998 | Jannard et al. |
| D398,330 S | 9/1998 | Lin |
| 5,815,235 A * | 9/1998 | Runckel ....................... 351/92 |
| D399,238 S | 10/1998 | Simioni |
| D399,866 S | 10/1998 | Yee |
| D401,610 S | 11/1998 | Flanagan |
| D404,754 S | 1/1999 | Yee et al. |
| D407,099 S | 3/1999 | Wang |
| D407,427 S | 3/1999 | Matera |
| D408,839 S | 4/1999 | Matera |
| D408,841 S | 4/1999 | Conway |
| D409,224 S | 5/1999 | Matera |
| D410,022 S | 5/1999 | Conway |
| D414,796 S | 10/1999 | Arnette |
| 5,963,296 A | 10/1999 | Matera |
| D420,035 S | 2/2000 | Hartman |
| D423,034 S | 4/2000 | Arnette |
| D423,550 S | 4/2000 | Matera |
| D423,551 S | 4/2000 | Lamy |
| D424,094 S | 5/2000 | Conway |
| D424,598 S | 5/2000 | Simioni |
| D425,102 S | 5/2000 | Matera |
| D425,103 S | 5/2000 | Yee et al. |
| 6,056,399 A * | 5/2000 | Jannard et al. .............. 351/126 |
| D427,227 S | 6/2000 | Conway |
| D427,622 S | 7/2000 | Conway |
| D428,907 S | 8/2000 | Matera |
| D429,754 S | 8/2000 | Markovitz et al. |
| D434,064 S | 11/2000 | Lane |
| D434,789 S | 12/2000 | Lane |
| 6,168,271 B1 | 1/2001 | Houston et al. |
| D441,002 S | 4/2001 | Stark et al. |
| 6,233,342 B1 | 5/2001 | Fernandez |
| D445,821 S | 7/2001 | Agnoli |
| 6,253,388 B1 | 7/2001 | Lando |
| 6,264,327 B1 | 7/2001 | Copeland |
| 6,282,727 B1 | 9/2001 | Lindahl |
| D449,640 S | 10/2001 | Grundy |
| D449,641 S | 10/2001 | Arnette |
| D450,744 S | 11/2001 | Rhoades et al. |
| D451,120 S | 11/2001 | Venezia |
| D452,522 S | 12/2001 | Chiou |
| D453,024 S | 1/2002 | Bonnemere |
| 6,334,680 B1 | 1/2002 | Larson |
| D453,783 S | 2/2002 | Ho |
| D456,038 S | 4/2002 | Arnette |
| D456,441 S | 4/2002 | Jannard et al. |
| 6,428,165 B1 | 8/2002 | Rivera |
| D464,669 S | 10/2002 | Thixton et al. |
| D469,459 S | 1/2003 | Moritz |
| D470,167 S | 2/2003 | Jannard et al. |
| D470,883 S | 2/2003 | Teng |
| D472,915 S | 4/2003 | Rohrbach et al. |
| D474,224 S | 5/2003 | Chen |
| D475,733 S | 6/2003 | Lee |
| D476,354 S | 6/2003 | Chen |
| 6,604,824 B2 | 8/2003 | Larson |
| 6,611,965 B1 | 9/2003 | Lee |
| 6,637,877 B1 * | 10/2003 | Hartley et al. ................. 351/44 |
| D481,751 S | 11/2003 | Stables |
| D483,393 S | 12/2003 | Chen |
| D487,477 S | 3/2004 | Lane |
| D488,499 S | 4/2004 | Mage |
| 6,715,873 B2 | 4/2004 | Nahmias |
| 6,767,095 B1 * | 7/2004 | Altelaar et al. ................. 351/59 |
| 6,783,235 B1 * | 8/2004 | Lin ............................ 351/62 |
| D496,064 S | 9/2004 | Mangum |
| D500,781 S | 1/2005 | Mage |
| D501,218 S | 1/2005 | Teng |
| 6,863,395 B1 * | 3/2005 | Teng ........................ 351/103 |
| D513,518 S | 1/2006 | Stables |
| D515,617 S | 2/2006 | Stables |
| D515,618 S | 2/2006 | Stables |
| 7,011,404 B2 | 3/2006 | Howard et al. |
| D518,502 S | 4/2006 | Teng |
| D519,146 S | 4/2006 | Yasuhara |
| D519,148 S | 4/2006 | Wu |
| 7,036,927 B2 | 5/2006 | Kopfer |
| D525,278 S | 7/2006 | Krefman |
| D532,438 S | 11/2006 | Yang |
| D533,892 S | 12/2006 | Moody et al. |
| D534,569 S | 1/2007 | Teng |
| D534,573 S | 1/2007 | Mage |
| D534,942 S | 1/2007 | Lynch |
| D535,316 S | 1/2007 | Teng |
| D535,317 S | 1/2007 | Wolfe |
| D535,682 S | 1/2007 | Paulson |
| D536,028 S | 1/2007 | Paulson |
| D537,861 S | 3/2007 | Teng |
| D537,863 S | 3/2007 | Markovitz |
| D538,326 S | 3/2007 | Guo |
| D539,330 S | 3/2007 | Hester |
| D539,834 S | 4/2007 | Hester |
| D540,370 S | 4/2007 | Sheldon |
| D540,846 S | 4/2007 | Sheldon |
| D541,839 S | 5/2007 | Sheldon |
| D542,330 S | 5/2007 | Elmore |
| D543,572 S | 5/2007 | Yee et al. |
| D544,018 S | 6/2007 | Huang |
| D544,521 S | 6/2007 | Lee |
| D545,348 S | 6/2007 | Chen |
| D545,872 S | 7/2007 | Yee et al. |

| | | | | | |
|---|---|---|---|---|---|
| D545,873 S | 7/2007 | Sheldon | D570,900 S | 6/2008 | Markovitz |
| D546,867 S | 7/2007 | Teng | D572,294 S | 7/2008 | Markovitz |
| D547,794 S | 7/2007 | Jannard et al. | D572,748 S | 7/2008 | Markovitz |
| D548,269 S | 8/2007 | Baden et al. | D575,323 S | 8/2008 | Jannard et al. |
| D548,769 S | 8/2007 | Chen | D575,813 S | 8/2008 | Li |
| D549,268 S | 8/2007 | Daems et al. | D580,475 S | 11/2008 | Markovitz et al. |
| D549,746 S | 8/2007 | Popov | D581,449 S | 11/2008 | Yee |
| D549,764 S | 8/2007 | Teng | D581,450 S | 11/2008 | Moritz |
| D550,272 S | 9/2007 | Markovitz | D583,853 S | 12/2008 | Markovitz et al. |
| D550,753 S | 9/2007 | Li | D584,758 S | 1/2009 | Mage |
| D550,755 S | 9/2007 | Fuchs | D584,759 S | 1/2009 | Yang |
| D550,757 S | 9/2007 | Li | 7,481,529 B1 * | 1/2009 | Chen .......................... 351/83 |
| D552,155 S | 10/2007 | Markovitz | D585,928 S | 2/2009 | Markovitz |
| D552,665 S | 10/2007 | Mage | D586,380 S | 2/2009 | Yee |
| D553,177 S | 10/2007 | Chen | D588,183 S | 3/2009 | Friedman |
| D553,663 S | 10/2007 | Moody | D588,626 S | 3/2009 | Markovitz |
| D554,687 S | 11/2007 | Arnette | D589,079 S | 3/2009 | Markovitz et al. |
| D554,689 S | 11/2007 | Jannard et al. | D590,433 S | 4/2009 | Lane et al. |
| D555,705 S | 11/2007 | Chuang | D594,052 S | 6/2009 | Yang |
| D556,243 S | 11/2007 | Elmore | D595,333 S | 6/2009 | Markovitz et al. |
| D556,245 S | 11/2007 | Lane | D597,124 S | 7/2009 | Markovitz |
| D556,246 S | 11/2007 | Yee | D599,837 S | 9/2009 | Markovitz et al. |
| D556,248 S | 11/2007 | Elmore | D600,271 S | 9/2009 | Markovitz et al. |
| D557,324 S | 12/2007 | Moody | D603,446 S | 11/2009 | Moody |
| D557,730 S | 12/2007 | Mage | D603,447 S | 11/2009 | Markovitz et al. |
| D557,731 S | 12/2007 | Mage | D603,448 S | 11/2009 | Markovitz |
| D558,816 S | 1/2008 | Yee | D606,112 S | 12/2009 | Markovitz et al. |
| D559,301 S | 1/2008 | Elmore | D606,575 S | 12/2009 | Markovitz et al. |
| D561,809 S | 2/2008 | Yee | D606,578 S | 12/2009 | Markovitz et al. |
| D561,810 S | 2/2008 | Fox et al. | D606,580 S | 12/2009 | Markovitz et al. |
| D561,812 S | 2/2008 | Fox et al. | 7,648,233 B2 * | 1/2010 | Blanshay et al. .............. 351/47 |
| D561,813 S | 2/2008 | Baden et al. | 2006/0238698 A1 | 10/2006 | Sheldon |
| D561,814 S | 2/2008 | Thixton et al. | 2006/0268218 A1 | 11/2006 | Medana |
| D563,455 S | 3/2008 | Markovitz | 2007/0261155 A1* | 11/2007 | Tabacchi ....................... 2/439 |
| D565,087 S | 3/2008 | Yee et al. | 2010/0085533 A1* | 4/2010 | Calilung et al. ............... 351/90 |
| D568,921 S | 5/2008 | Anderl | | | |
| D568,924 S | 5/2008 | Markovitz | * cited by examiner | | |

GOGGLES WITH INTERCHANGEABLE LENS

FIELD OF THE INVENTION

The present invention relates in general to sports goggles such as goggles for skiing, off-road motorcycling (MX), snowboarding and ATV riding. More specifically, it relates to a pair of snow or MX goggles with pivoting upper and lower members mounted on a frame that enables the lens to be easily removed and replaced.

BACKGROUND OF THE INVENTION

In recent years there has been a tremendous growth in the use of protective, safety and sports eyewear. Examples are ski goggles and safety glasses worn in industrial settings. The lens portion of the goggles receives the greatest amount of wear and damage and they regularly become scratched and broken. This often occurs in sporting applications where the user falls while wearing the goggles or when the lens becomes scratched or cracked, therefore needing replacement. For various reasons, it is economically desirable to replace the lens portion of the eyewear when needed rather than replacing the entire article. There are also applications in which the lens needs to be interchanged with a different type of lens given a change of circumstance or environment. For example, different types of tinted lenses are used by skiers given different ambient lighting conditions such as sunny versus cloudy days.

Most commercially available goggles which provide the functionality of lens interchangeability utilize a flexible elastomeric ring which encircles the lens. To remove the lens, it must be pried from a groove in the surrounding ring. This is a difficult and time-consuming procedure which is hard to perform without a tool other than one's fingers. This can be even more frustrating when the lens removal and replacement needs to be accomplished outdoors where tools are not available.

There have been attempts disclosed in the patent art to provide goggles with interchangeable lenses to satisfy this need. Examples include U.S. Pat. No. 5,815,235 issued to Runckel entitled "Ski Goggles with Pivotal Frame Members for Interchanging Lenses." This patent discloses a pivoting lower frame member which opens the encasement of a single lens that then may be easily extracted and replaced. The problem with this design, however, is that the lens is not sufficiently supported, and firm capture of the lens within the frame members is dependent upon excessive compression from the frame elements which often loosen, leading to a loss of sufficient grip on the lens.

Another attempt at providing sports eyewear with an interchangeable lens is the safety eyeglasses disclosed in U.S. Pat. No. 7,011,404 issued to Howard et al. entitled "Safety Glasses with Pivoting Interchangeable Single-Lens." This document discloses a substantially rigid frame with a snap-in lens which pivots into and out of a locked position. In addition, a nose bridge portion or the center of the browbar may include a locking mechanism for holding the lens in position. While such eyewear provides an easily interchangeable lens, it does not provide adequate eye protection or stability required of sports ski goggles.

There is therefore a need in the art for goggles which include a lens that is easily interchangeable. There is a further need for goggles with an interchangeable lens system that does not require additional tools. And finally, there is a need in the art for goggles with an easily interchangeable lens system which is durable and economical to manufacture.

SUMMARY OF THE INVENTION

In order to meet the needs in the art described above, the present goggles have been devised. In one embodiment, a full-coverage pair of goggles protects the eyes of the wearer and includes a continuous contoured inner perimeter of its frame which is adapted to fit snugly against the wearer's face at all points. The present invention utilizes a substantially rigid frame with separate top and bottom individually rotatable elements, namely an upper browbar and a lower nosepiece, that firmly capture the lens from above and below. The lens is further secured to the frame by projections on each of the browbar and nosepiece which fit through apertures in the lens. At the top, a post which projects forwardly from the frame is received in the well of the browbar by snap-fit engagement. At the bottom, a prong on the rotatable nosepiece passes through a bottom aperture of the lens and is received in a recess of a bottom portion of the frame by snap-fit engagement. The apertures and cooperating projections are preferably located along the center of a one-piece lens. Thus, the rotatable browbar and nosepiece capture the lens top and bottom by edgewise compression as well as securely holding the lens front-to-back through the lens apertures. This system provides a means of mechanically attaching the lens that permits the quick and easy release of the lens from the frame yet providing secure attachment of the lens to the frame when the browbar and nosepiece are in their closed and locked positions.

In one embodiment of the invention used for skiing, side portions of the frame include vent holes on the side portions which allow the free flow of ambient air to the interior of the goggles behind the lens. Furthermore, the lens may be of a two-layer type in which a front and back lens plate is separated by a gap to create an air space which serves to thermally insulate the inside surface of a lens to help prevent fogging.

It is therefore an object of the invention to provide a sport goggle such as ski goggles which provide ease of lens interchangeability in a rugged structure which can resist a violent impact without damage or breakage. It is a further object of the invention to provide a pair of ski goggles with an interchangeable lens system which is easy and quick requiring minimal dexterity of the user. Further objects and advantages will become apparent from the following further description and drawings which depict a preferred embodiment.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DESCRIPTION OF THE PREFERRED EMBODIMENT

Figure 1:
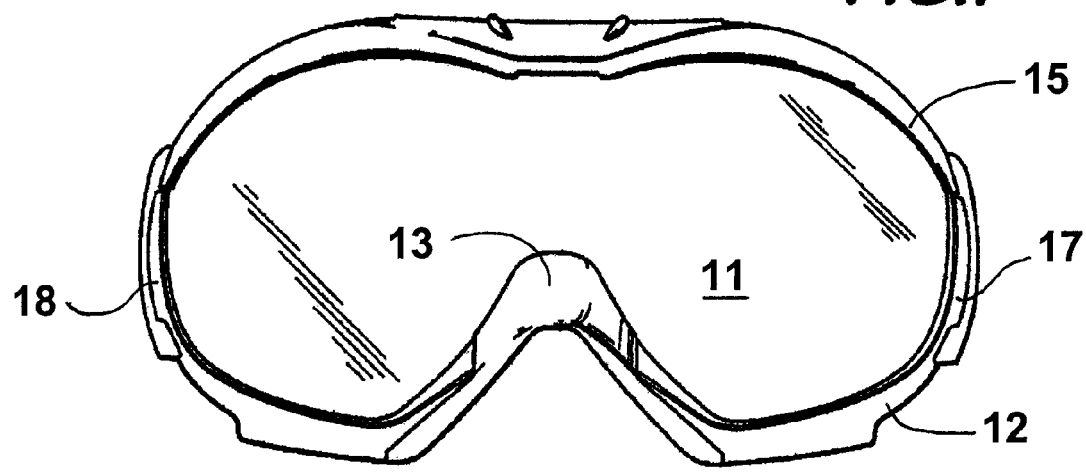
FIG. 1 is a front elevation view.

Referring now to FIG. 1, an embodiment of the present invention depicted is a pair of ski goggles which include the basic elements of a substantially rigid frame 12 which holds a lens 11. As will be further described herein, the lens is secured by rotatable elements browbar 15 and nosepiece 13. Ventilation ducts 17 and 18 provide ventilation for the interior of the goggles.

Figure 2:
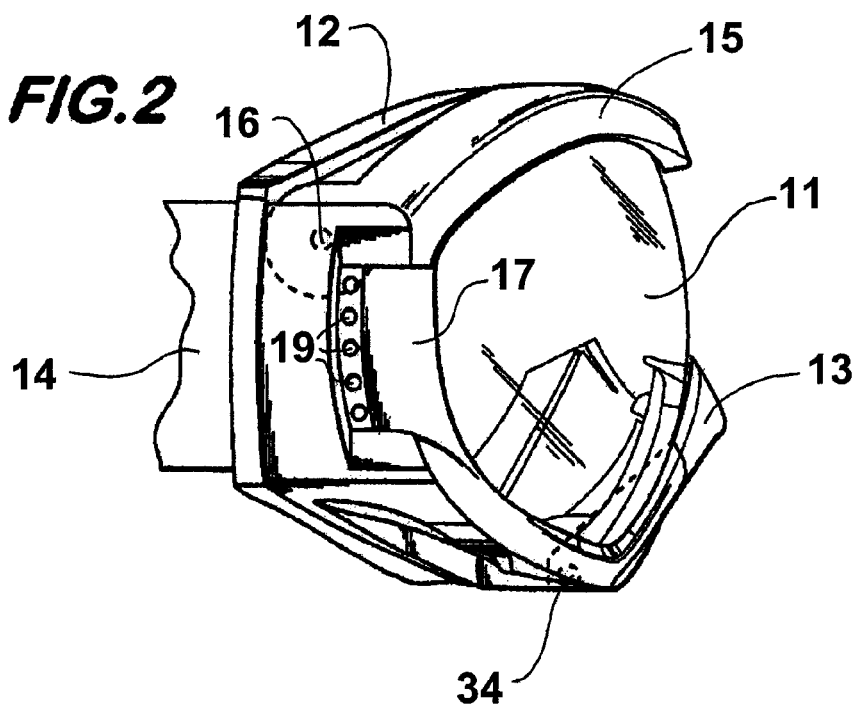
FIG. 2 is a left side elevation view.

Referring now to FIG. 2, only the right side region is shown in this figure but it is sufficient to fully depict the embodiment since the goggles are substantially symmetrical about a vertical centerline through the lens 11, the left side being a mirror image of the right side. The browbar 15 is rotatably affixed to frame 12 by way of a pin hinge 16 at side regions of the frame. Nosepiece 13 is likewise rotatably affixed to frame 12 at a bottom portion of the frame. The nosepiece is rotatably affixed to the frame by way of laterally projecting axles 34 on either side of the nosepiece. The axles 34 are received in compatible bushings of the frame. The frame is preferably composed of a molded high-density plastic and is a unitary substantially rigid structure having a continuous and contoured inner perimeter that fits snugly against the wearer's face. The frame 12 is held in position on the wearer's head by means of flexible elastic strap means 14. Ventilation duct 18, like duct 17 on the other side of the frame, is provided with vent holes 19 which supply a flow of air to the interior of the goggles behind the lens.

Figure 3:
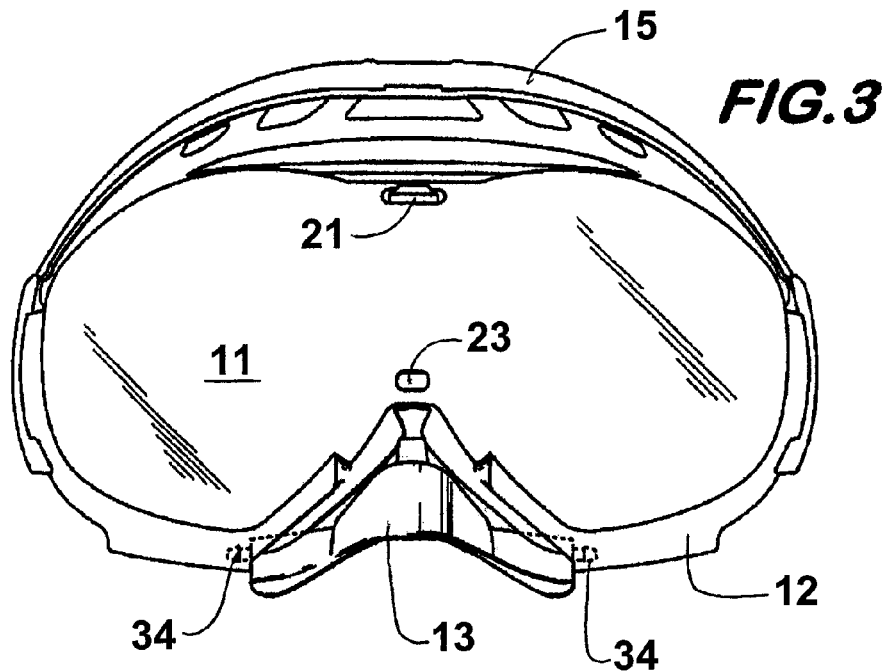
FIG. 3 is a front elevation view with the browbar and nosepiece in their open positions.

Referring now to FIG. 3, a front view of the goggles is shown. Here the browbar 15 and nosepiece 13 are in their open positions where the lens 11 is free to release from the goggle frame 12. The lens includes upper aperture 21 and lower aperture 23 that receive projections from the frame and nosepiece, respectively, to enhance the securement of the lens to the frame. Nosepiece 13 is rotatably affixed to the lower portion of the frame by way of axles 34 which project laterally from either side of the nosepiece and are received within corresponding recesses molded into frame 12 on opposite sides of the nosepiece.

Figure 4:
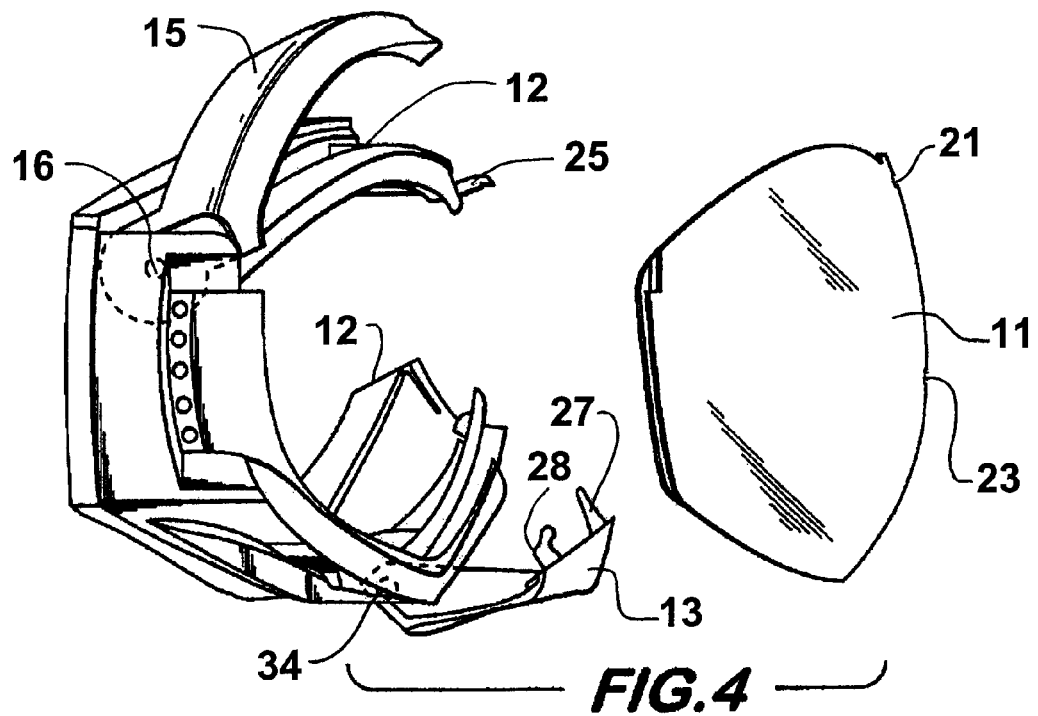
FIG. 4 is a left side exploded view with the lens removed.

Referring now to FIG. 4, greater detail of the lens-to-frame securement system is depicted. A post 25 projects from the top edge of frame 12 and is positioned to be received by upper aperture 21 of lens 11. Similarly, when lens 11 is in its assembled position and nosepiece 13 is rotated to its closed position, nosepiece prong 27 extends through the lower aperture 23. The nosepiece 13 is securely held in its closed position by locking snap-fit engagement of claw 28 which engages a compatible recess in the bottom portion of the frame.

Figure 5:
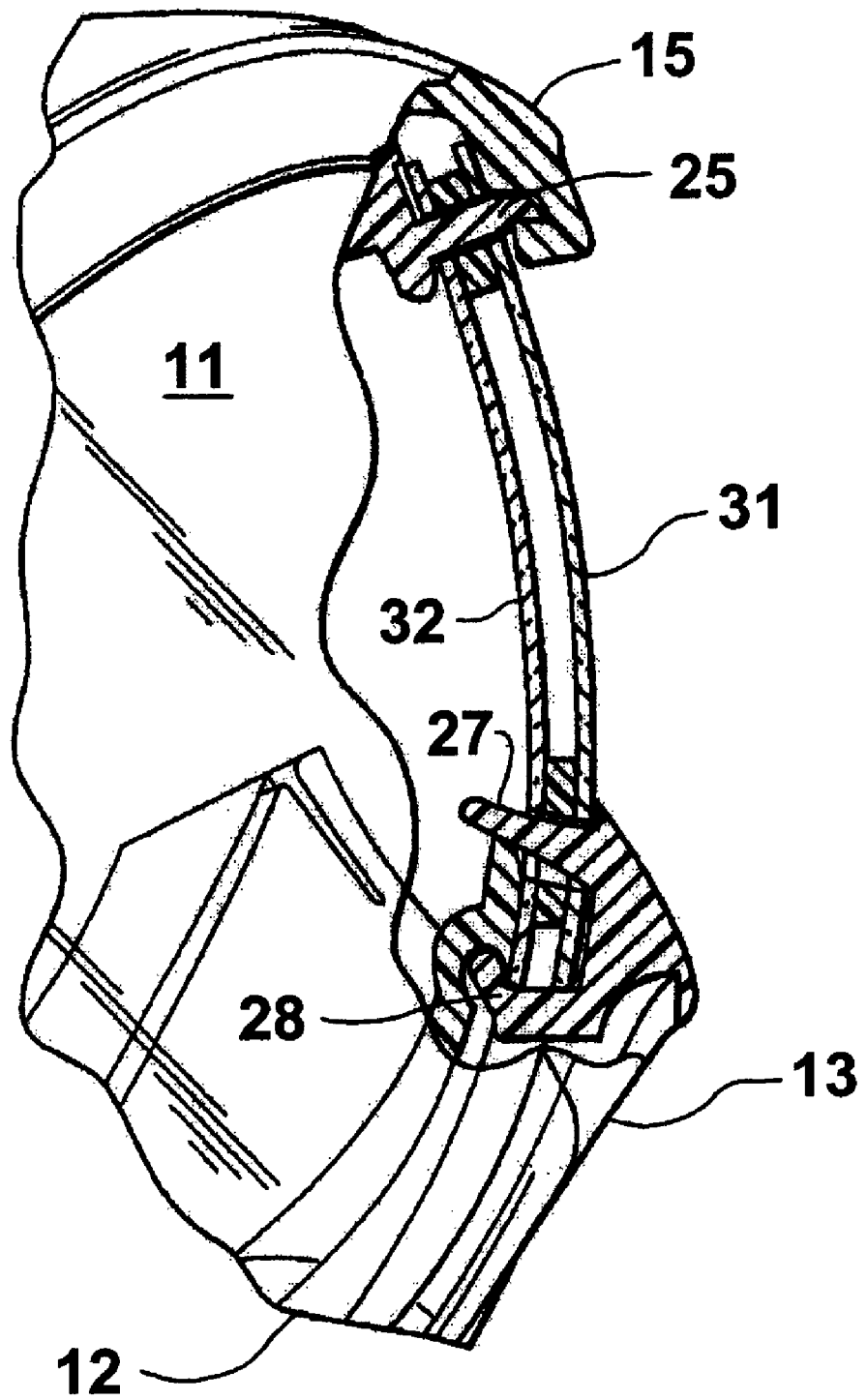
FIG. 5 is a left side partial sectional view with the browbar and nosepiece in their closed positions.

Referring now to FIG. 5, the goggles are shown with lens 11 in its installed position with browbar 15 and nosepiece 13 in their closed position surrounding the top and bottom edges of the lens respectively. Frame post 25 is received within a well of the browbar 15 along the top edge of the lens while nosepiece prong 27 is fitted through the lower aperture of the lens. The nosepiece as a unit is held in locked snap-fit engagement with the frame by virtue of the resilience of prong 27 and locking claw 28 which is received in a recess in the lower portion of the frame. The lens is thus held firmly by the locking snap-fit engagement of the browbar 15 and nosepiece 13 with the frame 12. As shown in this figure, lens 11 is of two-piece construction, including a front lens plate 31 and rear lens plate 32 which are separated by a spacer. This construction provides airspace between the plates for thermal insulation between the interior surface of the lens assembly and the outer surface in order to help prevent fogging. The lenses are cut from flat-sheet material and then heat-formed to shape, laminated by inserting a die to shape an open-cell foam piece with an adhesive between the lenses and pressed together. Yet greater detail of these lens-engaging constructions is shown in the following FIG. 6.

Figure 6:
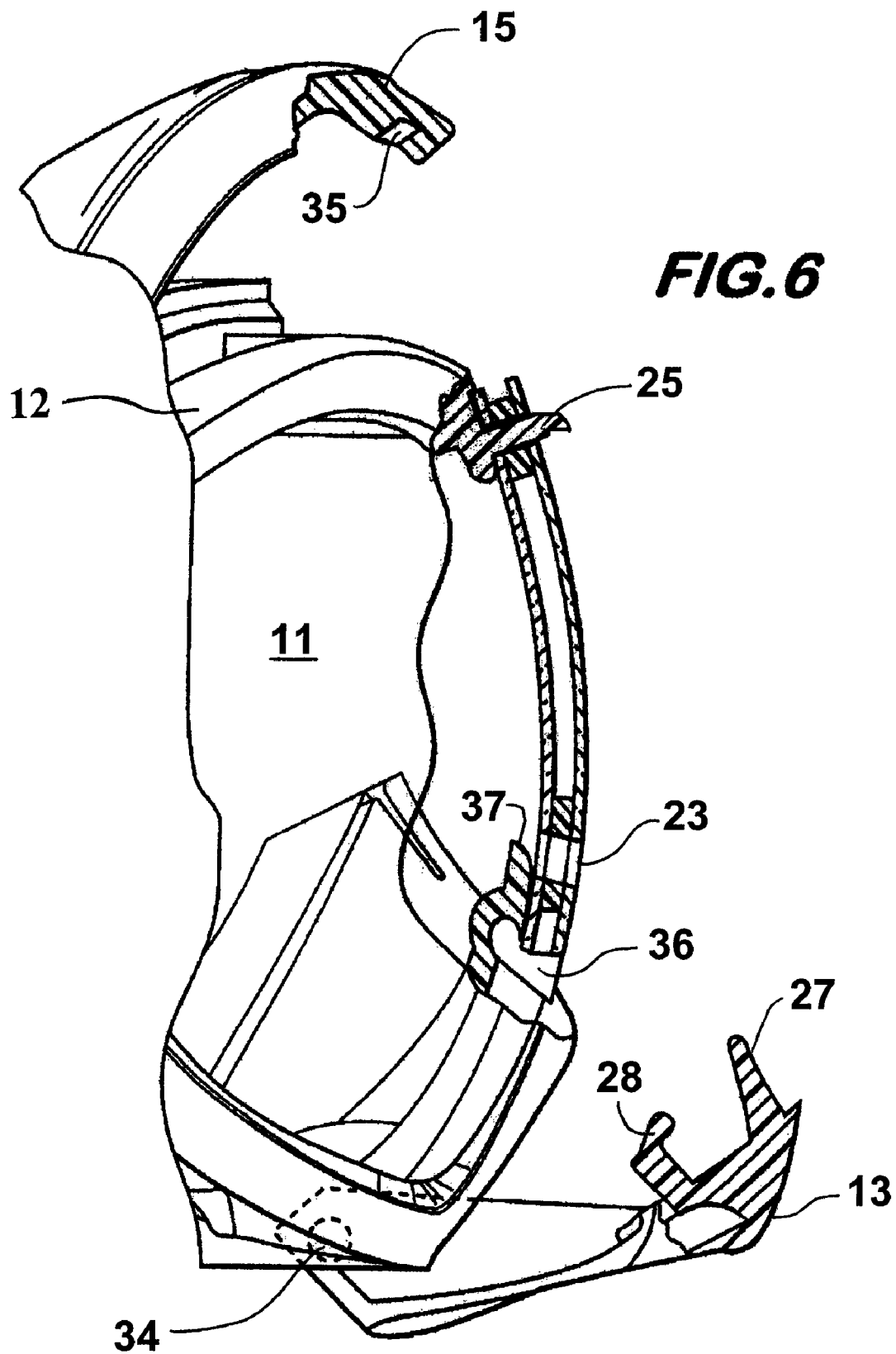
FIG. 6 is a left side partial sectional view with the browbar and nosepiece in their open positions.

Referring now to FIG. 6, the goggles are shown in the same position as depicted in FIG. 5 except that browbar 15 and nosepiece 13 are shown in their open positions. Nosepiece 13 is rotatably connected to the lower portion of the frame by axle means 34. Browbar 15 includes a well 35 which receives frame post 25 while lower portion of the frame 12 includes a lip 37 which in conjunction with recess 36 secures nosepiece projections 27 and 28 in closed and locking snap-fit positions. The snap-fit action of these components is owing to the resilience of the projecting elements which deform temporarily when being moved to their position of full engagement.

The operation of the goggles shown in the preferred embodiment depicted in FIGS. 1-6 above, with particular attention to FIG. 6, may be carried out as follows. To remove the lens 11, the nosepiece 13 is first opened and unclipped from the frame 12 by placing a finger on the underneath area of the nose bridge and pulling gently straightaway from the front of the goggle until the nosepiece 13 rotates into the fully open position. Next, the browbar 15 is unclipped from the frame centerpost 25 by grasping the browbar in the front underneath edge and gently pulling straight up until the browbar 15 releases from the frame and rotates into the fully open position. The lens 11 is then removed by gently grasping the top edge of the lens and sliding the bottom edge of the lens upward out of a groove in the bottom portion of the frame 12. The goggles are now ready to receive the replacement lens.

The new lens can now be installed by sliding it vertically down into the groove in the lower portion of a groove in the frame 12 until the lens is seated in the groove. The lens is properly seated when the lower aperture 23 is in alignment with the prong-receiving lip 37 in the lower portion of the frame 12. The browbar 15 is now rotated over the top edge of the lens until the browbar flexes slightly securing itself over the frame centerpost 25, blocking the lens into position as the centerpost is received in the well 35 of the browbar, thus completing the process of lens replacement.

This process is extremely convenient, easy to perform, and requires no tools. There is very little force applied to the lens and therefore it is very unlikely to be damaged during the replacement process. It will therefore be appreciated that the above-stated objects of the invention have been achieved by the detailed description of the preferred embodiment provided above.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention as claimed.

The Invention claimed is:

1. Goggles, comprising:
  a substantially rigid, unitary goggle frame configured to extend around the eyes and between the wearer's temples at two side regions to fit against a wearer's face, said frame having means adapted to receive and hold a lens;
  a unitary browbar rotatably connected to said frame at said side regions and movable between an open and a closed position, said browbar engaging said lens along a top edge thereof when moved downward to the closed position of the browbar; and
  a nosepiece rotatably connected to a bottom portion of said frame and movable between an open and a closed position engaging said lens along a bottom edge thereof when rotated upward to the closed position of the nosepiece.

2. The goggles of claim 1 wherein said lens is manually removable from said frame when said browbar and said nosepiece are rotated to their respective open positions.

3. The goggles of claim 2 wherein said frame includes a centerpost which receives an upper aperture in the lens adjacent the top edge.

4. The goggles of claim 3 wherein said browbar includes a well for receiving said centerpost when said browbar is in its closed position.

5. The goggles of claim 4 wherein said nosepiece includes a prong extending through a lower aperture in said lens when said nosepiece is in its closed position, said prong being withdrawn from said lower aperture when said nosepiece is rotated to its open position.

6. The goggles of claim 5 wherein said upper aperture is a single aperture located in the center of the lens.

7. The goggles of claim 6 wherein said lower aperture is a single aperture located in the center of the lens.

8. The goggles of claim 1 wherein the frame centerpost is received in the well of the browbar to secure the browbar in its closed position by locking snap-fit engagement.

9. The goggles of claim 1 wherein said nosepiece prong is received in a recess of the bottom portion of said frame by locking snap-fit engagement when said nosepiece is in its closed position.

10. The goggles of claim 1 further including a continuous contoured inner perimeter of the frame adapted to fit against the wearer's face at all points along the perimeter.

11. The goggles of claim 1 wherein said lens comprises two spaced plates.

12. The goggles of claim 1 further including lateral ventilation ducts integral with the frame on either side of the goggles adjacent the side regions.

13. The goggles of claim 1 further including a plurality of vent holes within the ventilation ducts, providing fluid communication between each of the ducts and an interior space of the goggles behind the lens.

* * * * *